United States Patent [19]

Friary et al.

[11] Patent Number: 5,034,531
[45] Date of Patent: Jul. 23, 1991

[54] FUSED POLYCYCLIC PYRANYL COMPOUNDS AS ANTIVIRAL AGENTS

[75] Inventors: Richard J. Friary, West Orange; John H. Schwerdt, Lake Hiawatha; Ashit K. Ganguly, Upper Montclair, all of N.J.

[73] Assignee: Schering Corporation, Kenilworth, N.J.

[21] Appl. No.: 289,285

[22] Filed: Dec. 23, 1988

[51] Int. Cl.$^5$ .............. C07D 221/02; C07D 221/18; C07D 221/06; C07D 311/26
[52] U.S. Cl. ........................ 546/116; 546/62; 546/64; 546/83; 546/89; 546/318; 548/256; 548/255; 549/383; 549/384
[58] Field of Search ............... 546/116; 514/302; 544/333, 182, 405

[56] References Cited

U.S. PATENT DOCUMENTS 3,518,273 6/1970 Strandtmann et al. ............. 546/116

FOREIGN PATENT DOCUMENTS 0178633 4/1986 European Pat. Off. .

OTHER PUBLICATIONS

Sliwa et al., J. Heterocyclic Chem. 16, 939–44 (1979).
Sliwa et al., Chem. Abs., vol. 91, No. 23, entry #192526z (1979).
Villani et al., "Benzopyranopyridine Derivatives", Journ. Med. Chem., vol. 18, No. 1, pp. 1–8 (1975).
Villani et al., "Benzopyranopyridine Derivatives", Journ. Org. Chem., vol. 40, No. 12, pp. 1734–1737 (1975).

Primary Examiner—Mark L. Berch
Assistant Examiner—E. C. Ward
Attorney, Agent, or Firm—Henry Jeanette; Joseph T. Majka

[57] ABSTRACT

Novel polycyclic pyranyl compounds, pharmaceutical compositions, and their use as anti-viral agents are disclosed.

5 Claims, No Drawings

FUSED POLYCYCLIC PYRANYL COMPOUNDS AS ANTIVIRAL AGENTS

BACKGROUND OF THE INVENTION

The present invention relates to novel polycyclic pyranyl compounds that possess anti-viral activity and to pharmaceutical compositions and methods for using such compounds and compositions.

F.J. Villani, T.A. Mann, E.A. Wefer, J. Hannon, L.L. Larca, M.J. Landon, W. Spivak, D. Vashi, S. Tozzi, G. Danko, M. del Prado, and R. Luis (J. Med. Chem. 18, 1 (1975)) and F.J. Villani, J. Hannon, E.A. Wefer, T.A. Mann and J.B. Morton (J. Org. Chem. 40, 1735 (1975)) disclose the structures of 5H-[1]benzopyrano[2,3-b]pyridin-5-one and 10H-[1]-benzopyrano[3,2-b]pyridine-10-one. European Patent Application 178,633 filed Oct. 15, 1985 discloses 2-phenylpyrano[2,3-b]pyridines active against a variety of viruses. It would be desirable to provide alternate compounds, especially polycyclic pyranyl compounds to treat against viruses.

SUMMARY OF THE INVENTION

The present invention is directed to a compound of formula 1.0

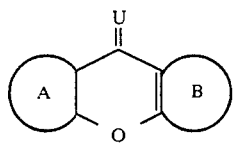

1.0 or a pharmaceutically acceptable salt or solvate thereof, wherein:
U represents O or S;

represents a ring selected from

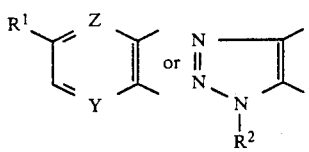

wherein
$R^1$ is hydrogen, alkyl, halogen, hydroxy, or alkoxy;
$R^2$ is aryl, aromatic heterocyclic, alkyl, aralkyl, or heteroalkyl; and
Z and Y independently represent nitrogen or CH; and wherein

 represents

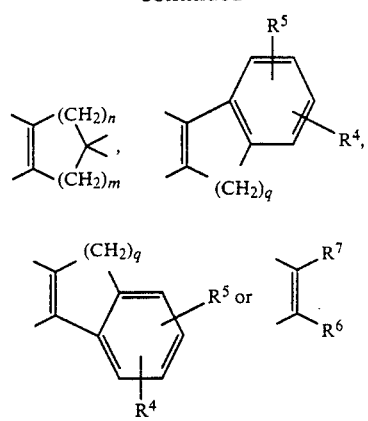

in which

is $NR^3$, $S(O)_p$ (wherein p is zero, 1 or 2), O, or a single bond joining $(CH_2)_n$ to $(CH_2)_m$ and $R^3$ is H, alkyl, aralkyl, heteroalkyl, or acyl;
$R^4$ and $R^5$ independently represent hydrogen, halogen, alkyl, hydroxyl, alkoxy, —O—acyl, amino or substituted amino or a salt thereof, or —NH—acyl;
$R^6$ is H, alkyl, aralkyl, or aromatic heterocyclic;
$R^7$ is H, alkyl, aralkyl, aryl or aromatic heterocyclic;
m and n independently represent 0, 1, 2, 3, 4, 5 or 6 wherein m+n is 3 or more when X is a single bond and m+n is 2 or more when X is other than a single bond; and
q is 1, 2, 3, or 4.

Preferably, U is oxygen. Also preferred are those compounds of formula 1.0 wherein U is oxygen and

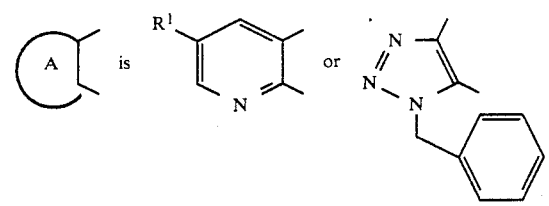

wherein $R^1$ is hydrogen or halogen.

Also preferred are compounds (1.0) wherein U is oxygen and

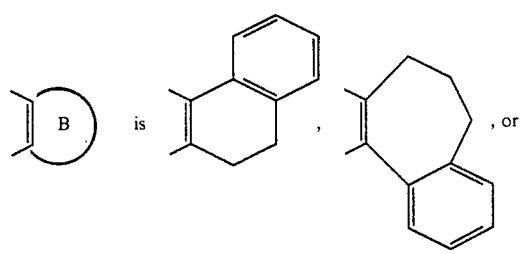

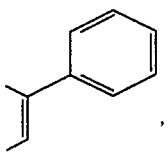

Also preferred are those compounds (1.0) wherein U is oxygen and

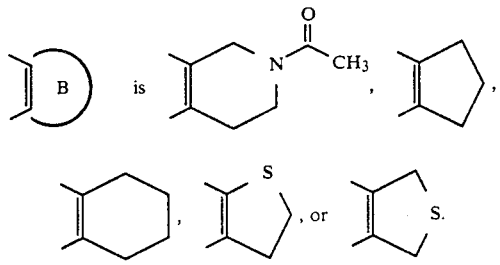

The present invention is also directed to a pharmaceutical composition comprising a pharmaceutically effective amount of a compound of formula 1.0 in combination with a pharmaceutically acceptable carrier.

In addition, the present invention is directed to a method of treating susceptible viral infections in a mammal comprising administering to said mammal an antiviral effective amount of a compound of formula 1.0, defined hereinbefore.

When utilized in the present specification and in the appended claims, the terms listed hereinbelow unless otherwise indicated are defined as follows:

The term "alkyl" refers to a straight or branched saturated hydrocarbon moiety (i.e. hydrocarbons having carbon-carbon single bonds) containing from 1 to 6 carbon atoms, for example, methyl (i.e. —CH₃), ethyl, propyl, isopropyl, butyl, isobutyl, tert-butyl, pentyl, hexyl and the like The term "alkoxy" refers to an alkyl moiety containing from 1 to 6 carbon atoms covalently bonded to an adjacent structural element through an oxygen atom, such as for example, ethoxy (i.e. —OCH₃), ethoxy, propoxy, isopropoxy, butoxy, pentoxy, hexoxy and the like.

The terms "halogen" and "halo" refers to fluoride, chloride, bromide or iodide.

The term "acyl" refers to a carbonyl moiety

bonded to a hydrogen, alkyl, aryl, alkoxy, amino, substituted amino, aromatic heterocyclic or an aryloxy group such as a formyl moiety

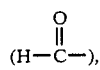

an alkanoyl moiety

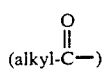

of one to six carbon atoms in the alkyl portion, a heteroyl moiety

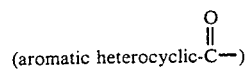

of 2 to 14 carbon atoms, an aroyl moiety

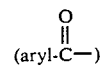

of six to fifteen carbon atoms in the aryl portion, an ester moiety

of one to six carbon atoms in the alkoxy portion, an amide moiety

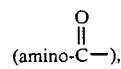

or an aryloxy acyl moiety. Typical acyl groups include acetyl, benzoyl, ethoxycarbonyl and the like.

The term "amino" refers to the primary amine (—NH₂).

The term "substituted amino" refers to a secondary or a tertiary amine wherein each hydrogen is or can be substituted by an alkyl moiety of 1 to 4 carbon atoms or by an aryl moiety of 6 to 15 carbon atoms, which moieties can be same or different.

The term "aryl" refers to a carbocyclic moiety containing at least one benzenoid-type ring, with the aryl groups preferably containing from 6 to 15 carbon atoms, for example, phenyl, naphthyl, indenyl, indanyl, and the like. Optionally, the aryl moiety can be substituted by one or more substituents such as halo, alkyl, alkoxy, nitro and the like, as illustrated by 4-chlorophenyl, 2-fluorophenyl, 4-nitrophenyl, 3-methylphenyl, 3,5-dichlorophenyl and the like.

The term "aralkyl" refers to an aryl moiety of 6 to 15 carbon atoms covalently bonded to an alkyl moiety of 1 to 6 carbon atoms such as, for example, benzyl, phenylethyl, and the like.

The term "aromatic heterocyclic" refers to a cyclic moiety having at least one O, S and/or N hetero atom interrupting the ring structure and having a sufficient number of unsaturated carbon to carbon double bonds, or nitrogen to carbon double bonds to provide aromatic character, with the aromatic heterocyclic groups preferably containing from 2 to 14 carbon atoms, for example, 2-, 3- or 4-pyridyl, 2- or 3-furyl,, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, and the like. Such heterocyclic groups can be bonded via various positions on the ring and all such variations are contemplated.

The term "heteroalkyl" refers to an aromatic heterocyclic moiety of 2 to 14 carbon atoms as defined hereinbefore, covalently bonded to an alkyl moiety of one to six carbon atoms.

The invention also includes pharmaceutical compositions containing pharmaceutically effective amounts of a compound of formula 1.0 as well as a method of treating virus infections using the appropriate pharmaceutical compositions.

DETAILED DESCRIPTION OF THE EMBODIMENTS

Certain compounds of formula 1.0 can exist in different isomeric as well as conformational forms. The present invention contemplates all such isomers both in pure form and in admixture, including racemic mixtures.

The compounds of formula 1.0 can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of the invention.

Certain compounds of formula 1.0 are acidic in nature, e.g. those compounds which possess a phenolic hydroxyl group. These compounds may form pharmaceutically acceptable salts. Examples of such salts may include salts of alkali and alkaline earth metals such as sodium, potassium, lithium, cesium, calcium or barium; as well as aluminum, gold and silver salts. Also contemplated are salts formed with pharmaceutically acceptable amines such as ammonia, alkyl amines, hydroxyalkylamines, N-methylglucamine and the like.

Certain basic compounds of formula 1.0 also form pharmaceutically acceptable salts, e.g., acid addition salts and quaternary ammonium salts Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms can be regenerated by treating the salt with a suitable dilute aqueous base solution such as dilute aqueous sodium hydroxide, potassium carbonate, ammonia or sodium bicarbonate. The quaternary ammonium salts are prepared by conventional methods, e.g., by reaction of a primary or secondary amino group in a compound of formula 1.0 with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention.

Processes for Preparation

In the processes for preparing the compounds of formula 1.0, generally the reactants are contacted in amounts and under conditions effective to yield the desired compound of formula 1.0. The reactants can be contacted at temperatures ranging from about 0 to about 150 degrees Centigrade (° C.), preferably from about 70 to about 120° C., most preferably from about 100 to about 110° C. The contacting is performed at ambient pressures although pressures greater or less than ambient can be employed. The contacting of the reactants can be carried out for about 5 minutes to about 72 hours or more until the reaction is substantially completed, preferably from about 1 hour (hr) to about 48 hours. Also preferred is that the reactants are stirred during the contacting procedures. About equimolar amounts of the reactants can be employed, although lesser or greater amounts of either reactant can be employed.

After the reaction is completed, the desired compound 1.0 can be recovered by conventional separatory and recovery methods such as phase separation, distillation or evaporation of any solvents present, crystallization, chromatography, filtration and the like.

The compounds of formula 1.0 can be prepared by processes (a) through (h) below, wherein $R^1$, $R^2$, $R^3$, $R^4$, $R^5$, $R^6$, $R^7$, X, Y, Z, m, n, p, and q are as defined hereinbefore, unless stated otherwise.

Process (a): A compound of formula 2.1, which can be obtained from process (i) hereinafter, can be contacted with a suitable base to produce a compound of formula 1.1:

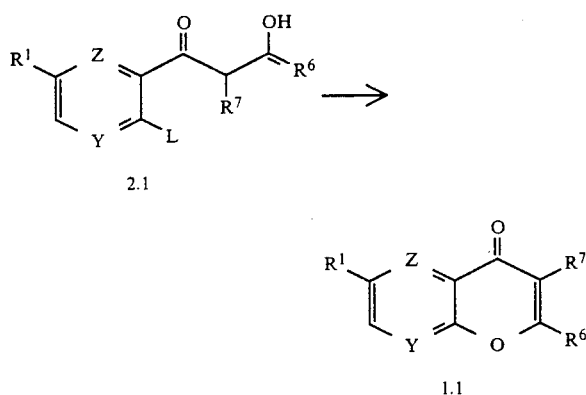

wherein L represents a leaving group which can be halogen, such as chloro or bromo, —O-alkyl, —S-alkyl, —OSO$_2$-aryl such as —OSO$_2$-phenyl, —OSO$_2$-2,4,6-trimethylphenyl, —OSO$_2$-2,4,6-triisopropylphenyl and —OSO$_2$-alkyl such as —OSO$_2$-hexyl.

Suitable bases for the reaction of process (a) are of the formula M$^+$$^-$T in which M$^+$ is sodium (Na$^+$) potassium (K$^+$), or lithium (Li$^+$) and $^-$T is a suitable counter-ion which can be $^-$O-alkyl of 1 to 6 carbon atoms, $^-$N(i-Pr)$_2$, $^-$N(Si(CH$_3$)$_3$)$_2$, or $^-$OC(CH$_3$)$_3$($^-$OBu-t). Preferably the base is Li$^+$$^-$N(SiMe$_3$)$_2$ or M$^+$$^-$O-alkyl, most preferably potassium t-butoxide (K$^+$$^-$OBu-t.)

Process (a) can be carried out in any suitable solvent, including ethereal solvents, such as diethyl ether, 1,2-dimethoxyethane, and tetrahydrofuran; dipolar aprotic solvents, such as N,N-dimethylformamide and dimethyl sulfoxide; and alcoholic solvents such as methanol, ethanol, propanols, and butanols. Preferably the solvent is an alcohol, most preferably t-butanol (HOBu-t.) The reaction of process (a) can be carried out at temperatures ranging from about zero degrees Centigrade (0° C.) to the boiling point of the solvent used, preferably between ambient and 50° C., more preferably at the boiling point of the solvent employed.

Process (b): A compound of formula 2.2, which can be obtained from process (j) hereinafter, is contacted with an aqueous acid to produce a compound of formula 1.2:

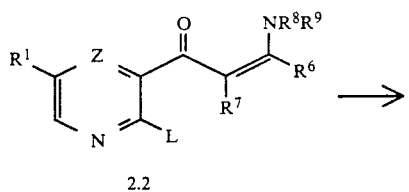

2.2

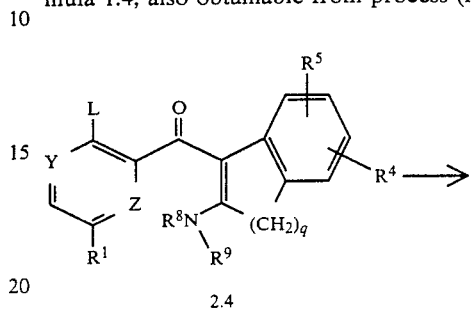

1.2 wherein $R^1$, Z, L, $R^6$, $R^7$ are as defined hereinabove, and $R^8$ and $R^9$ independently represent alkyl or, taken together, preferably, a closed chain (i.e., ring) of atoms, e.g., $-(CH_2)_4-$, $-(CH_2)_2O(CH_2)_2-$, or the like.

Suitable aqueous acids which can be employed as the proton source and also as the solvent for the reaction of process (b) above include organic aqueous acids such as acetic, trifluoroacetic, paratoluenesulfonic, methanesulfonic acid or mixtures thereof; and inorganic aqueous acids such as hydrochloric (HCl) or sulfuric acid ($H_2SO_4$). Aqueous in-organic acids are preferred, most preferably hydrochloric acid. The aqueous acids can be employed in catalytic or excess amounts such as 6 Normal(N) HCl.

Water-miscible or water-immiscible co-solvents can be used with the aqueous acid in process (b). Suitable water-miscible co-solvents include C-1 to C-4 alcohols such as methanol, ethanol, and propanols; and ethers, such as tetrahydrofuran, 1,4-dioxane or 1,2-dimethoxyethane, preferably ethanol. Suitable waterimmiscible co-solvents include aromatic hydrocarbons, such as benzene, toluene, and the like, preferably benzene. The reaction of process (b) can be carried out at temperatures similar to those described for process (a), hereinabove.

Process (c): A compound of formula 2.3, which can be obtained from process (k) below, can be contacted with a suitable aqueous acid to produce a compound of formula 1.3, also obtainable from process (e):

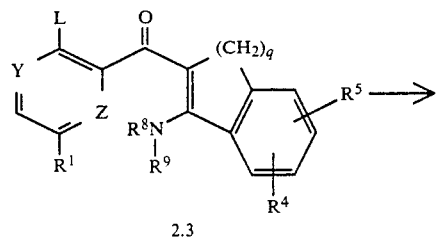

2.3

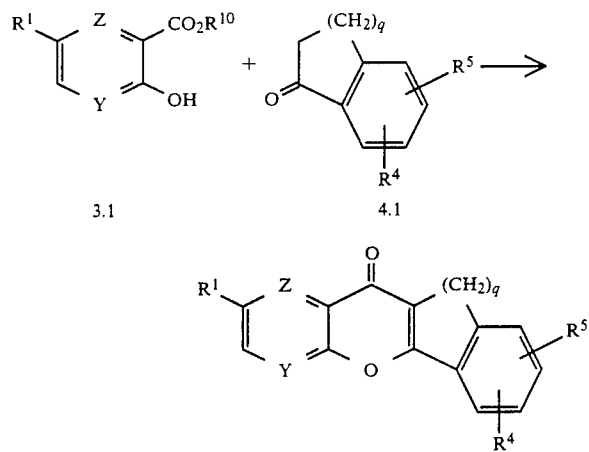

1.3 wherein L, Y, Z, $R^1$, $R^4$, $R^5$, $R^8$, $R^9$ and q are as defined hereinbefore.

The acids, co-solvents, and temperatures used to carry out the reaction of process (c) are similar to those described for process (b).

Process (d): A compound of formula 2.4, which can be obtained from process (l) below, can be contacted with an aqueous acid to produce a compound of formula 1.4, also obtainable from process (f):

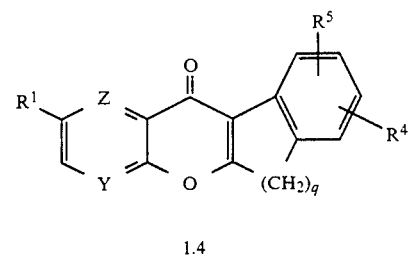

2.4

1.4 wherein L, Y, Z, $R^1$, $R^4$, $R^5$, $R^8$, $R^9$ and q are as defined hereinbefore.

The acids, co-solvents, and temperatures used to carry out the reaction of process (d) are similar to those described for process (b).

Process (e): A compound of formula 3.1 is contacted with a compound of formula 4.1 and an acid to produce a compound of formula 1.3:

3.1      4.1

1.3 wherein Y, Z, $R^1$, $R^4$, $R^5$ and q are as defined hereinbefore.

In formula 3.1 above, the group $R^{10}$ represents alkyl or hydrogen.

Acids suitable for carrying out the reaction of process (e) include inorganic acids, such as polyphosphoric; and organic acids, such as trifluoroacetic, trifluoromethanesulfonic, methanesulfonic, and Eaton's reagent (a mixture of phosphorous pentoxide and methanesulfonic acid in a ratio of 1 to 10 by weight).

Process (e) can be carried out with a solvent or neat (without a solvent), preferably neat. Where a solvent is employed, suitable solvents include aromatic hydrocarbons, such as benzene, toluene, preferably xylenes, and the like; or halocarbons, such as 1,2-dichloroethane or 1,2-dichlorobenzene. The reaction of process (e) can be carried out at temperatures ranging from about 0° C. to the boiling point of the solvent employed, preferably from about ambient to about 50° C. If the reaction is carried out neat, the temperature is preferably about 120° C.

Process (f): A compound of formula 3.1 is contacted with a compound of formula 4.2 and an acid to produce a compound of formula 1.4:

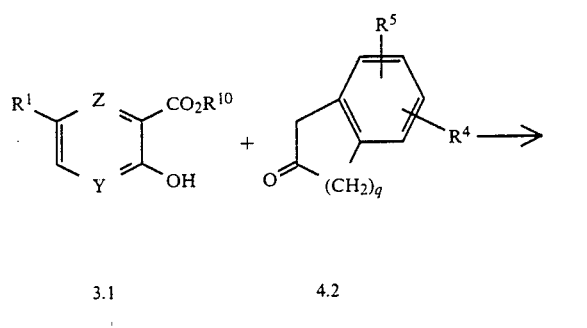

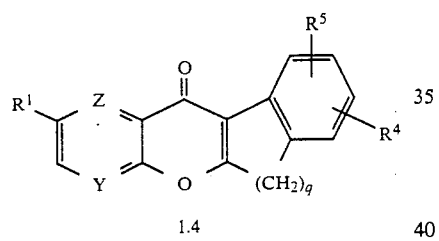

wherein Y, Z, $R^1$, $R^4$, $R^5$, $R^{10}$ and q are as defined hereinbefore.

The acids, temperatures, and solvents for carrying out the reaction of process (f) are similar to those described for process (e).

Process (g): A compound of formula 2.5, which can be obtained by process (m) below, can be contacted with a suitable base to produce a compound of formula 1.5:

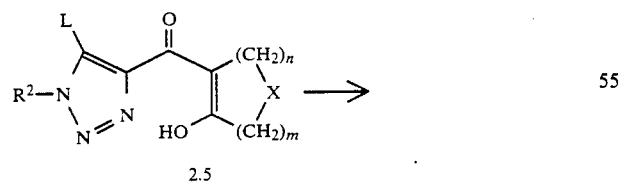

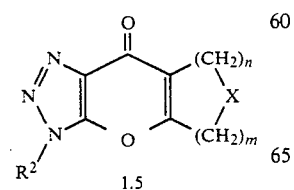

wherein L, X, $R^2$, m and n are as defined hereinbefore.

The bases, solvents, and temperatures used to carry out the reaction of process (g) are similar to those used in process (a), before.

Compounds of formula 1.0 wherein

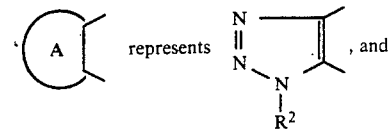

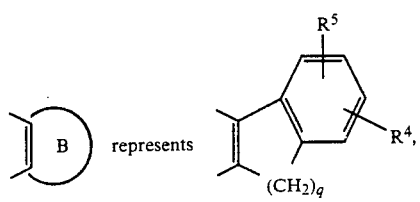

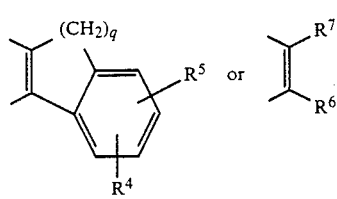

wherein $R^2$, $R^4$, $R^5$, $R^6$, $R^7$ and q are as defined hereinbefore can be prepared as described in process (g).

Compounds of the formula 1.0 wherein

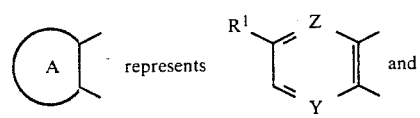

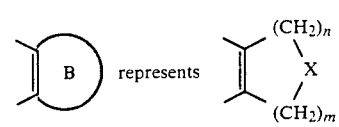

wherein Y is N and X, $R^1$, Z, m and n are defined hereinbefore can be prepared as described in processes (a) or (b). In compounds, wherein Y is CH, and X, $R^1$, Z, m and n are as defined hereinbefore, compounds 1.0 can be prepared as described in process (b).

Process (h) A compound of formula 1.6 below, wherein

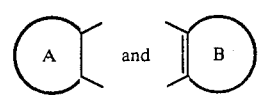

are as defined hereinbefore and represent, in part, compounds 1.1–1.5 before, from processes (a) through (g) above, can be contacted with a sulfurating agent to produce a compound of formula 1.7:

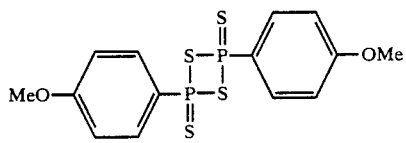

1.6

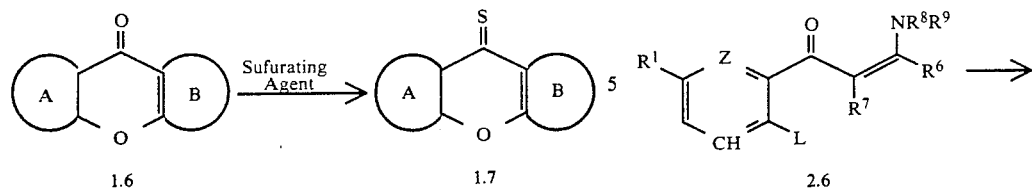

1.7

A suitable sulfurating agent is phosphorus pentasulfide ($P_2S_5$), or Lawesson's reagent, which has the structure:

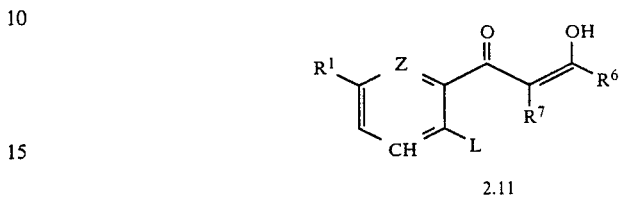

The reaction can be carried out at temperatures ranging from 0° C. to 200° C., preferably in aromatic or heterocyclic solvents like toluene or pyridine.

Such methods for sulfurating can be found in J. March (ed.). Advanced Organic Chemistry, Reactions, Mechanisms and Structure, 3rd Edition, John Wiley & Sons, New York, NY pp. 793-795, whose preparative teachings are incorporated herein by reference.

Preparation of Starting Materials

The starting materials and methods used to prepare the compounds of formula 1.0 are known to skilled practitioners in the art. The following is a listing of selected preparative intermediate compounds as well as references disclosing methods for making such intermediates:

morpholine enamine of acetaldehyde: Chem. Ber. (1957), 90, pp. 229;
morpholine enamines of tetrahydrothiophene-3-one: Rec. Trav. Chim. (1964), 83, pp. 1160;
5-chloro-1-(phenylmethyl)-1,2,3-triazol-4-carbonyl chloride: J. Heterocyclic Chem. (1985), 22, pp. 77, and
(2-chloro-3-pyridinyl)[2-(1-pyrrolidinyl)-cyclopenten-1-yl]methanone: International Appln. No. PCT/US 86/01269

Other intermediate enamine compounds which can be used to make compounds of the present invention can be prepared by methods similar to those described in "Enamines in Organic Synthesis", Chapter 8 in "Enamines", ed. A.G. Cook, Marcel Dekker, New York and London, 1969, pp. 313-468 and in "Enamines" 2nd ed., ed. A. Gilbert Cook, Marcel Dekker, Inc., New York and Basel, 1988, pp. 103-164. The preparative teachings of these references are incorporated herein by reference.

The starting materials of formulas 2.1, 2.2, 2.3, 2.4 and 2.5 can be prepared by processes (i)-(m) below. Compounds 2.6 and 2.7 can be prepared by processes (n) and (o) below.

Process (i) A compound of formula 2.6, which can be obtained from process (n) below, can be contacted with water in the presence of an acid catalyst to produce a compound of formula 2.11:

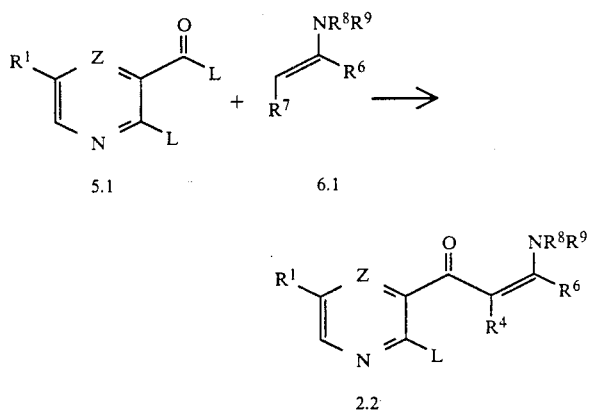

wherein L, Z, $R^1$, $R^6$, $R^7$, $R^8$, and $R^9$ are as defined hereinbefore.

Acids, co-solvents, and temperatures used to carry out the reaction of process (i) are similar to those described for process (b) above.

Process (j): In the presence of a base and under reaction conditions described hereinbelow, a compound of formula 5.1 can be contacted with an enamine compound of formula 6.1 to produce an intermediate compound or starting material of formula 2.2:

wherein L, Z, $R^1$, $R^6$, $R^7$, $R^8$ and $R^9$ are as defined hereinbefore.

The general reaction for process (j) above, and that for processes (k), (l), (n), and (o) below, which are enamine acylations, are known to those skilled in the art and are further described in "Enamines" (2nd ed., ed. A. Gilbert Cook, Marcel Dekker, Inc., New York and Basel, 1988, pp. 204-215), as well as International Appl. No. PCT/US86/01269 or International Publication No. WO86/07359, 18 December 1986, whose preparative teachings are incorporated herein by reference.

Process (k): In the presence of a base, and under reaction under conditions as described in "Enamines" and in PCT/US 86/01269, supra, a compound of formula 5.1 can be contacted with a enamine compound of formula 6.2 to produce the intermediate compound of formula 2.3:

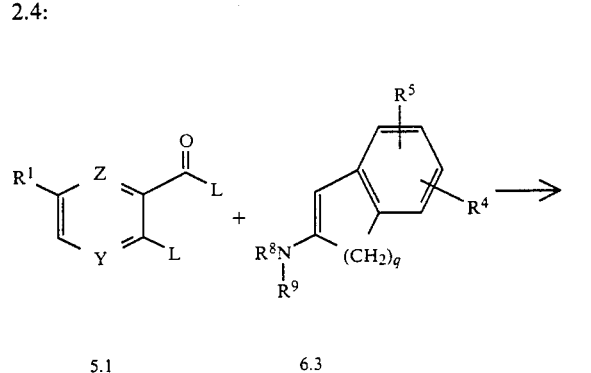

5.1          6.2

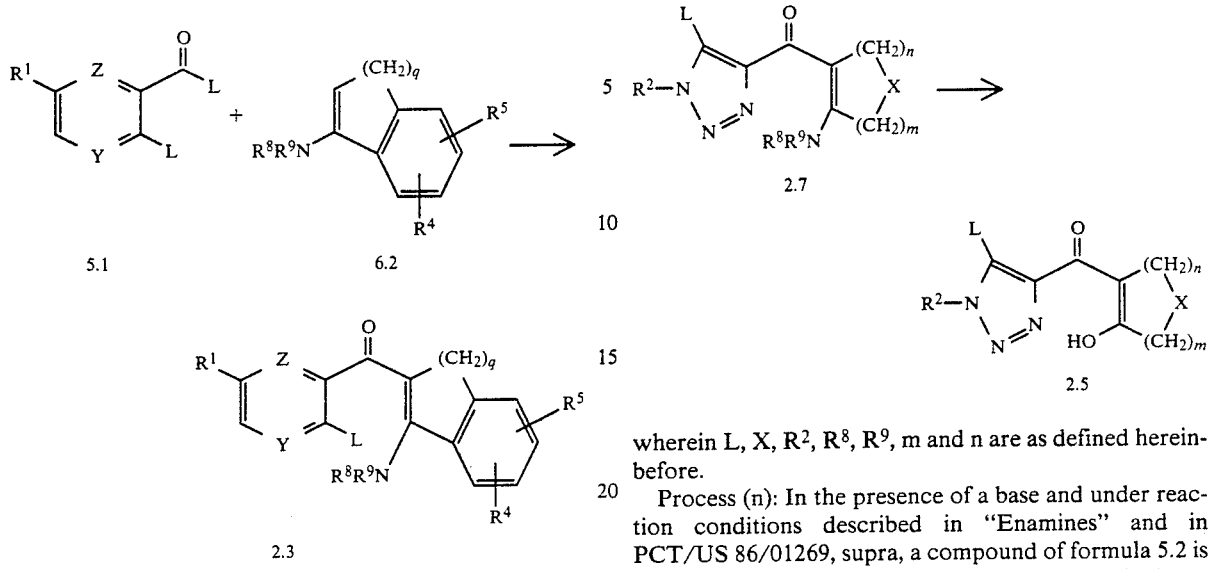

2.7

2.5 wherein L, X, $R^2$, $R^8$, $R^9$, m and n are as defined hereinbefore.

Process (n): In the presence of a base and under reaction conditions described in "Enamines" and in PCT/US 86/01269, supra, a compound of formula 5.2 is contacted with a enamine compound of formula 6.1 to produce an intermediate compound of formula 2.6:

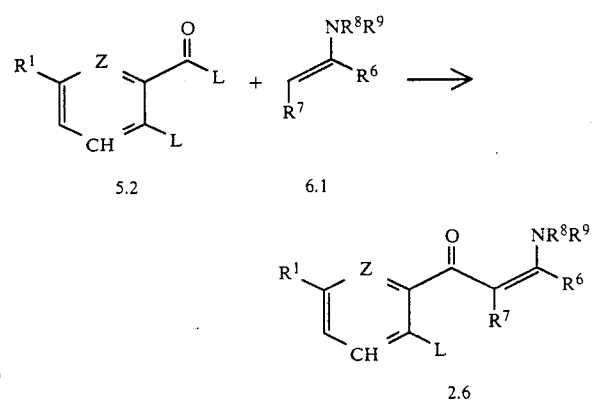

5.2          6.1

2.6 wherein each L, Z, Y, $R^1$, $R^4$, $R^5$, $R^8$, $R^9$ and q is as defined hereinabove.

Process (1): In the presence of a base and under reaction conditions described in "Enamines" and in PCT/US 86/01269, supra, a compound of formula 5.1 can be contacted with a enamine compound of formula 6.3 to produce the intermediate compound of formula 2.4:

wherein L, Z, $R^1$, $R^6$, $R^7$, $R^8$ and $R^9$ are as defined hereinbefore.

Process (o): In the presence of a base and under reaction conditions described in "Enamines" and in PCT/US 86/01269, supra, a compound of formula 5.3 can be contacted with a enamine compound of formula 6.4 to produce an intermediate compound of formula 2.7:

5.1          6.3

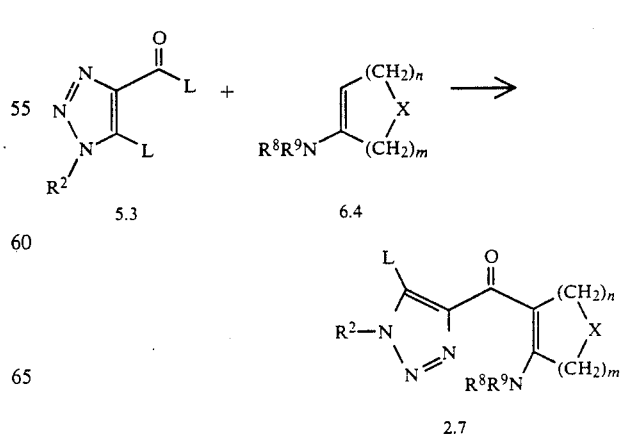

5.3          6.4

2.4

2.7 wherein L, Y, Z, $R^1$, $R^4$, $R^5$, $R^8$, $R^9$ and q are as defined hereinbefore.

Process (m): A compound of formula 2.7, obtained from process (o), can be contacted as in process (i) and under reaction conditions described in process (i), to produce a compound of formula 2.5:

wherein L, X, $R^2$, $R^8$, $R^9$, m and n are as defined hereinbefore.

The following examples illustrate the compounds of the present invention in a manner of which they can be prepared or practiced but, as such, should not be construed as limitations upon the overall scope of the same.

EXAMPLE 1

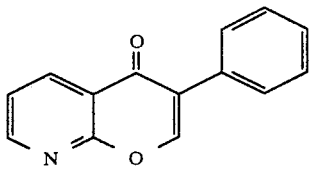

Add a solution of 3.52 grams (g) of 2-chloropyridine-3-carbonyl chloride in 20 milliliters (20 ml) of alcohol-free chloroform to a cooled (ice-acetone bath) solution containing 3.79 g of the morpholine enamine of phenylacetaldehyde, 3 ml of triethylamine and 20 ml of alcohol-free chloroform, all in an atmosphere of nitrogen. Stir the resulting mixture overnight, allowing it to warm to 25° C. Wash the solution sequentially with water, 1 Molar (M) sodium bicarbonate solution, and brine. Dry the organic solution, and concentrate it after filtering. Use the crude product directly in the next step.

Mix the residue with 6 N hydrochloric acid (50 ml per 4.50 g of residue), and stir the mixture at 25° C. for 24 hours. Extract the aqueous mixture with dichloromethane, and sequentially wash the combined extracts with water and brine. Dry the organic solution over sodium sulfate, filter, and concentrate to give a solid. Crystallize the solid to give 3-phenyl-4H-pyrano[2,3-b]pyridin-4-one, melting point (m.p.) 173°–176° C. (crystallized from ethyl acetate (EtOAc)).

EXAMPLE 2

By using similar procedures as in Example 1 and the appropriate 2-chloropyridine-3-carbonyl chlorides and enamines, the following compound is prepared:

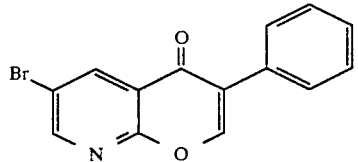

6-bromo-3-phenyl-4H-pyrano[2,3-b]pyridin-4-one, m.p. 193°–197° C. (crystallized from acetonitrile (MeCN)).

EXAMPLE 3

By using similar procedures as in Example 1 and the appropriate 2-chloropyridine-3-carbonyl chlorides and enamines, the following compound is prepared:

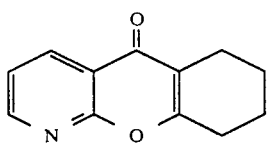

6,7,8,9-tetrahydro-5H-[1]-benzopyrano[2,3-b]pyridin-5-one, m.p. 139.0°–139.5° C. (crystallized from 2-propyl acetate (2-PrOAc)).

EXAMPLE 4

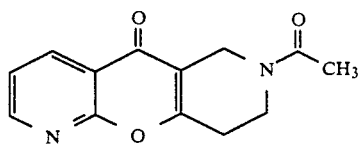

Add a solution of 2-chloropyridine-3-carbonyl chloride (17.9 g) in ethanol-free chloroform (90 ml) to a cooled (ice bath) solution of triethylamine (13.9 ml), the pyrrolidine enamine (19.4 g) of 1-acetyl-4-piperidone, and ethanol-free chloroform (90 ml). Ten minutes after completion of the addition, remove the ice bath; allow the mixture to stand at 25° C. overnight. Sequentially wash the red solution with water, 1M sodium bicarbonate solution, and with water. Dry the organic solution over sodium sulfate, and concentrate the filtered solution. Use the resulting red oil directly in the next step.

Dissolve the foregoing oil (11 g diluted to 60 ml with benzene) in a solution of benzene (60 ml) containing anhydrous para-toluenesulfonic acid (p-TsOH) (prepared from 6.34 g of p-TsOH monohydrate (p-TsOH.H$_2$O)). Reflux the resulting solution overnight, and then allow it to stand at 25° C. for two days. Evaporate the solvent and dissolve the residue in chloroform. Wash the solution sequentially with 1M sodium bicarbonate solution, 1N hydrochloric acid, and with water. Evaporate the solvent from the dried (sodium sulfate) solution, and triturate the residue with ethyl acetate. Collect the resulting solid on a filter, and purify it by chromatography on silica gel. Elute with methanol-dichloromethane (MeOH-CH$_2$Cl$_2$) (2:98 by volume) to give 7-acetyl-6,7,8,9-tetrahydro-5H-pyrano[2,3-b: 5,6-c']dipyridin-5-one, m.p. 181.5°–184.5° C. (crystallized from EtOAc).

EXAMPLE 5

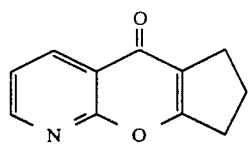

Reflux a mixture of (2-chloro-3-pyridinyl) [2-(1-pyrrolidinyl)cyclopenten-1-yl]methanone (13.8 g), p-TsOH.H$_2$O (9.51 g), and benzene (200 ml) for 44 hours. Cool the mixture, and evaporate the solvent. Dissolve the residue in chloroform and wash the solution sequentially with water, 1M sodium carbonate solution, water, 2N hydrochloric acid solution, water, and brine Filter the dried (sodium sulfate) solution and concentrate it. Chromatograph the residue over silica gel and elute the column with ethanol (EtOH)-stabilized chloroform (CHCl$_3$). Combine appropriate fractions, concentrate them, and crystallize the residue to give 7,8-dihydrocyclopentano[5,6]pyrano[2,3-b]pyridin-5(6H)-one, m.p. 98°–102° C. (crystallized from 2-PrOAc).

EXAMPLE 6

By using 1-(2-chloro-3-pyridinecarbonyl)-2-(1-pyrrolidinyl)-3,4-dihydronaphthalene, the following compound also can be prepared by essentially the same method as in Example 5:

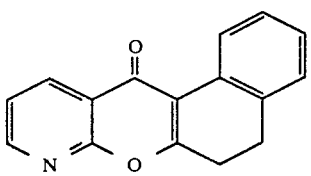

5,6-dihydro-12H-naphtho[1',2':5,6]pyrano[2,3-b]pyridin-12-one, eluted from silica gel by EtOH-stabilized CHCl₃, m.p. 125°-127° C. (crystallized from 2-PrOAc).

EXAMPLE 7

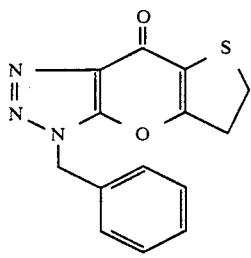

Stir a mixture of [5-chloro-1-(phenylmethyl)-1H-1,2,3-triazol-4-yl](2,3-dihydro-4-hydroxy-5-thienyl)methanone (3.25 g), potassium t-butoxide (1.70 g), and t-butanol (120 ml) under nitrogen in a 90° C. oil bath for 5 hrs. Evaporate the solvent and partition the residue between CH₂Cl₂ and water. Wash the CH₂Cl₂ solution sequentially with water and with 1N hydrochloric acid solution; dry the organic solution over magnesium sulfate, filter and concentrate it. Chromatograph the residue over silica gel and elute the column with CH₂Cl₂. Combine appropriate fractions, concentrate, and crystallize the residue to give 5,6-dihydro-3-(phenylmethyl)-thieno[2',3':5,6]pyrano[2,3-d]-1,2,3-triazol-8(3H)-one, m.p. 157°-160° C. (crystallized from MeCN).

EXAMPLE 8

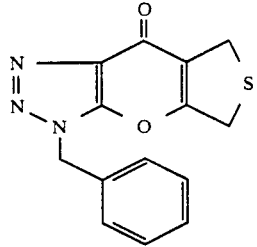

Add [5-chloro-1-(phenylmethyl)-1H-1,2,3-triazol-4-yl](2,5-dihydro-3-hydroxy-4-thienyl)methanon (2.89 g) to a solution of anhydrous p-TsOH (prepared from 1.7 g of p-TsOH H₂O) in benzene (50 ml) and reflux the resulting mixture for 28 hours. Cool the mixture, and sequentially wash it with 1M sodium bicarbonate solution, with 1N hydrochloric acid solution, and with water. Dry the organic solution over magnesium sulfate, and concentrate the filtered solution. Chromatograph the residue over silica gel, and elute the column with CH₂Cl₂-EtOAc (1:1). Combine fractions and evaporate the solvents to give 5,7-dihydro-3-(phenylmethyl)-thieno[3',4':5,6]pyrano[2,3-d]-1,2,3-triazol-8(3H)-one, m.p. 210°-212° C. (crystallized from MeCN).

EXAMPLE 9

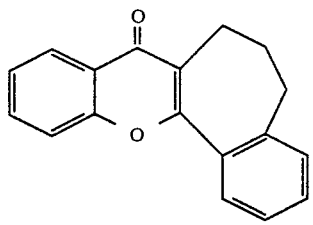

Stir a mixture of methyl salicylate (15.2 g), 1-benzosuberone (16.0 g), and polyphosphoric acid (100 ml) at 120° C. for about 14 hours. Pour the hot mixture over ice, stir 1 hour, and extract the aqueous mixture with chloroform. Sequentially wash the combined extracts with water, 1M sodium carbonate solution, and with brine. Dry the organic solution with sodium sulfate, and concentrate the filtered solution to give a black semisolid. Chromatograph the semi-solid over silica gel, elute the column with hexanes-dichloromethane (30:70), and concentrate combined fractions. Crystallize the residue to give 6,7-dihydrobenzo[b]benzo[3,4]cyclohepta[1,2-e]pyran-8(5H)-one, m.p. 139°-141° C. (crystallized from 2-PrOAc).

EXAMPLE 10

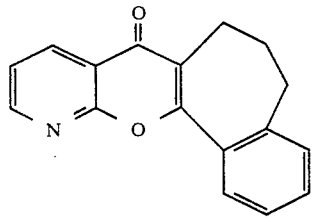

Over a period of 20 minutes, add a solution containing 2-chloropyridine-3-carbonyl chloride (7.04 g) in alcohol-free chloroform (43 ml) to a cooled (ice-acetone bath) solution of triethylamine (5.6 ml), the pyrrolidine enamine (8.54 g) of 1-benzosuberone, and alcohol-free chloroform (50 ml). Allow the mixture to warm to 25° C. overnight. Wash the solution sequentially with water and with brine; and dry the solution over sodium sulfate. Concentrate the solution to give an oil, and use the oil directly in the next step. Mix the oil with 6N hydrochloric acid (100 ml) and stir the mixture under nitrogen gas at 25° C. for 14 hours. Extract the aqueous solution with several portions of dichloromethane, and combine the extracts. Wash the combined extracts with water. Dry the organic solution with sodium sulfate, and concentrate the solution to give a tar. Chromatograph the tar over silica gel, and elute the column with dichloromethane. Evaporate the solvents, and crystallize the residue to give 6,7-dihydrobenzo[6',7']cyclohepta[2',1':5,6]pyrano[2,3-b]pyridin-8(5H)-one, m.p. 186.5°-189.5° C. (crystallized from EtOAc).

The examples which follow illustrate representative methods for preparing the starting materials for making the compounds of the present invention but, as such, should not be construed as limitations upon the overall scope of the same.

EXAMPLE 11

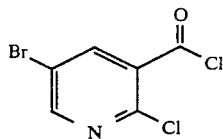

Add 8.5 g of anhydrous sodium acetate to a mixture of 13.8 g of 2-hydroxypyridinecarboxylic acid and 150 ml of acetic acid, stirred and heated, to a temperature between 45°–50° C. After 2–3 min., add 6.5 ml of bromine and heat the resulting mixture for 30 minutes to 80°–90° C. Add the mixture to 600 ml of water, stir for 15 minutes, and collect the dense precipitate on a filter. Wash the precipitate sequentially with water and with diethyl ether; dry the precipitate at 25° C. under about 0.5 millimeters (mm) of mercury (Hg) to give 5-bromo-2-hydroxypyridinecarboxylic acid, m.p. about 275°–280° C. (decomposes from 250° C.) (crystallized from water).

EXAMPLE 12

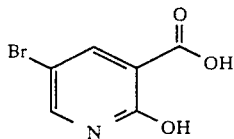

Add 25 ml of thionyl chloride and N,N-dimethylformamide (6 drops, about 0.3 ml) to 4.36 g of 5-bromo-2-hydroxypyridinecarboxylic acid and reflux the resulting mixture for 4 hours. Cool the mixture and concentrate it to give 5-bromo-2-chloro-3-pyridinecarbonyl chloride. The crude product can be used directly in the subsequent step.

EXAMPLE 13

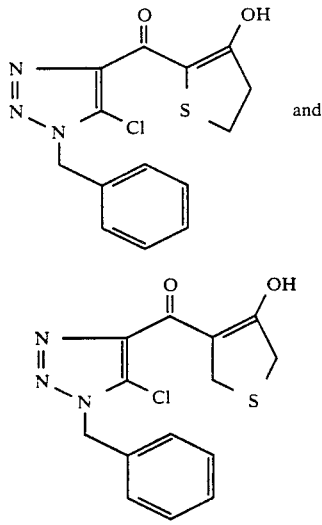

Add a solution of 20.9 g of 5-chloro-1-(phenylmethyl)-1,2,3-triazol-4-carbonyl chloride in 60 ml of $CH_2Cl_2$ to a mixture of the morpholine enamines (14.0 g) of tetrahydrothiophene-3-one and triethylamine (11.5 ml) cooled by dry ice bath. Stir the resulting mixture for 1 hour at −30° C. and for about 14 hours at 25° C. Wash the resulting solution with water and dry with magnesium sulfate. Evaporate the solvent, and chromatograph the residue over silica gel. Elute the column with $CH_2Cl_2$-EtOAc (9:1), combine appropriate fractions, and crystallize the residue from diethyl ether to give a mixture of the two desired products. Rechromatograph the mixture over silica gel, eluting with hexanes-$CH_2Cl_2$ (3:7 by volume) and combining fractions as appropriate. Crystallize the material that elutes first to give [5-chloro-1-(phenylmethyl)-1H-1,2,3-triazol-4-yl](2,5-dihydro-3-hydroxy-4-thienyl)methanone, m.p. 110°–113° C. (crystallized from dichloromethane/hexanes). Crysallize the material that elutes second to give [5-chloro-1-(phenylmethyl)-1H-1,2,3-triazol-4-yl](2,3dihydro-4-hydroxy-5-thienyl)methanone, m.p. 118°–120° (crystallized from $Et_2O$).

EXAMPLE 14

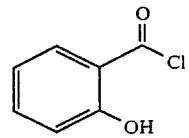

Add 11.8 g of oxalyl chloride dissolved in 25 ml of benzene to a suspension of 6.91 g of salicylic acid and 125 ml of benzene over a period of 20 minutes. Heat the mixture for about 14 hours, cool and evaporate the solvent to give 2-hydroxybenzenecarbonyl chloride as an oil. The crude product can be used directly in the subsequent step.

Antiviral Activity

The compounds of the present invention are active against certain DNA viruses such as herpes simplex virus. Thus, they show activity when tested in an in vitro activity assay, i.e. a plaque reduction assay which measures the ability of compounds to neutralize virus infectivity, e.g. herpes virus infectivity. The $IC_{50}$ value is the concentration of test compound in micrograms per milliliter (μg/ml) which results in a 50% decrease in viral gene expression compared to a non-treated control.

Thus, this invention includes within its scope pharmaceutical compositions comprising the compounds of this invention in admixture with a pharmaceutically acceptable carrier therefor. In addition, the present invention also provides methods of treating viral infections in warm blooded animals, including humans, having a viral infection and in need of treatment thereof. The present invention also provides a method of protecting uninfected warm blooded animals, including humans, which are susceptible to infection. The method comprises administering to said animal in need of such treatment or protection, an antiviral effective amount, of a compound of this invention or of a pharmaceutical composition thereof. In the foregoing compositions, the active compounds of this invention can be used alone as the sole active antiviral agent, or exist in combination with other therapeutic agents.

For the preferred oral administration, the compounds of this invention are typically formulated in the form of tablets, suppositories, capsules, elixirs, solutions, suspensions including liposome suspensions and the like, preferably solutions. For parenteral administration, the compounds of the present invention can be formulated into solutions or suspensions. Topical formulations such as lotions, creams, ointments, sprays and mechanical delivery devices, e.g. transdermal can also be used to deliver the compounds of the present invention.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene glycol polymers; betacyclodextrin; fatty alcohols, hydrolyzed cereal solids; water; polyalkylene glycols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgment of the attending clinician, upon a variety of factors. Such factors include the age and weight of the individual being treated, the mode of administration, the potency and lability of the administered compound, and the indication for which the drug is administered.

Typically, the dosage administered per day for treating viral infections will be oral administration of from about 1 mg/kg to about 75 mg/kg daily in single or divided doses, with about 1-25 mg/kg preferred.

The compounds of the invention can be administered as pharmaceutical compositions which may be administered topically, parenterally, or orally.

Such compositions can be prepared from standard ingredients using standard techniques. For example, topical compositions can be prepared using standard liquid formulations, such as oil-in-water or water-in-oil emulsions, and by using other physiologically acceptable carriers such as gelatin, vegetable oils, polyalkylene glycol or alcohol, and aerosols. Injectable formulations use aqueous physiologically acceptable carriers, e.g. distilled water.

Examples of compositions are as follows wherein the active ingredient is 3-phenyl-4-H-pyrano[2,3-b]-pyridin-4-one:

| Capsules: | Concentration | |
|---|---|---|
| Active Ingredient | 50 mg | 150 mg |
| Lactose USP | 106 | 73 |
| Corn Starch, Food Grade | 40 | 70 |
| Magnesium Stearate | 4 | 2 |

Blend the ingredients and fill into hard gelatine capsules.

| Oral liquid | Concentration |
|---|---|
| Active Ingredient | 50 mg |
| Sucrose | 800 |
| Glycerin | 0.4 |
| Water | qs. 1 ml. |

The following example illustrates the activities of various compounds for inhibiting beta-galactosidase.

EXAMPLE 15

Transient Expression Assay

Herpes simplex virus (HSV) is grown and titered on Vero cells, a standard cell line.

Plasmid pON 245 (constructed by Ed Mocarski at Stanford University, Stanford California) is used for the assay. This plasmid contains the HSV-1 thymidine kinase (TK) promoter located immediately 5' of the *E. coli* Lac Z gene and controls transcription from the bacterial gene in transient assays. Plasmids (22 $\mu$g/$10^6$ cells) are introduced into standard HeLa cells by DEAE-dextran-mediated transfection. DEAE-dextran is an electropositivity charged polymer which is a diethylamino ethyl ether of dextran. Forty-eight hours after transfection, cells are infected with HSV-2 (American Type Collection Culture (ATCC) VR-540) (multiplicity of infection=5 plaque-forming units per cell). Twenty-four hours after viral infection, levels of $\beta$-galactosidase in cells are assayed by incubation in the presence of 4-methylumbelliferyl-$\beta$-D-galactoside for 2 hours on a microfluorimeter after addition of 0.1 M glycine buffer, pH=10.3. The results of the assay are provided hereinbelow. An inhibitory concentration ($IC_{50}$ value), for example, of 8 $\mu$g/ml indicates the amount of compound which reduces maximal $\beta$-galactosidase expression by 50 percent. The inhibition of expression of $\beta$-galactosidase activity indicates the inhibition of viral replication at events prior to or including thiamine kinase (TK) expression by HSV-2.

TABLE 1

| $IC_{50}$-values for Inhibition of HSV replication | |
|---|---|
| Compound | $IC_{50}$-Values ($\mu$g/ml) |
| 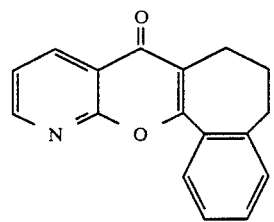 | >25 |
| 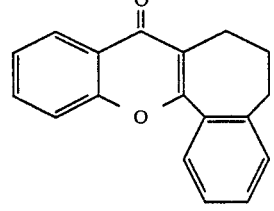 | 8 |
| 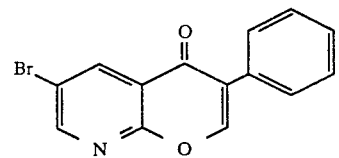 | 10 |

TABLE 1-continued

IC$_{50}$-values for Inhibition of HSV replication

| Compound | IC$_{50}$-Values (μg/ml) |
|---|---|
| 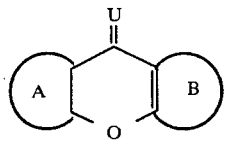 | 16 |
|  | 3 |
| 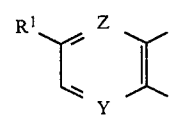 | 3 |
|  | 19 |
| 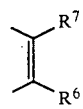 | 20 |
| (structure) | ≧25 |
| (structure) | 25 |

While the present invention has been described in conjunction with the specific embodiments set forth above, many alternative, modifications, and variations thereof will be apparent to those of ordinary skill in the art. All such alternatives, modifications and variations are intended to fall within the spirit and scope of the present invention.

What we claim is:

1. A compound of formula 1.0

(structure showing U, A, B, O)

or pharmaceutically acceptable salt or solvate thereof, wherein: U represents O or S;

(A ring) represents (structure with R$^1$, Z, Y)

wherein
R$^1$ is hydrogen, alkyl containing from 1 to 6 carbon atoms, halogen, hydroxy or alkoxy having from 1 to 6 carbon atoms; and Z is CH and Y is nitrogen; and wherein (B ring) represents (structure with R$^7$, R$^6$)

in which
R$^6$ is H, alkyl containing form 1 to 6 carbon atoms, aralkyl having an aryl moiety of 6 to 15 carbon atoms covalently bonded to an alkyl moiety of 1 to 6 carbon atoms, or an aromatic heterocyclic selected from the group consisting of:
(a) 2-, 3- or 4-pyridly;
(b) 2- or 3-furyl;
(c) 2- or 3-thienyl;
(d) 2-, 4-, or 5-thiazolyl;
(e) 3- or 5-(1,2,4-thiadiazolyl);
(f) 2-, 3-, 4-, 5-, 6- or 7-benzofuranyl;
(g) 2-, 3-, 4-, 5-, 6- or 7-indolyl; and
(h) 2-, 4-, or 5-oxazolyl; and
R$^7$ is aryl wherein said aryl is a carbocyclic moiety having at least one benzenoid ring and wherein said aryl group has from 6 to 15 carbon atoms.

2. The compound of claim 1 wherein U is oxygen.

3. The compound of claim 1 wherein U is oxygen and wherein R$^1$ is hydrogen or halogen.

4. The compound of claim 1 wherein U is oxygen and

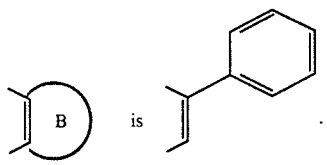
5. The compound of claim 1 which is:
3-phenyl-4H-pyrano[2,3b]pyridin-4-one, or
6-bromo-3-phenyl-4H-pyrano-[2,3-b]pyridin-4-one.
* * * * *